United States Patent
Yuzuriha

(10) Patent No.: US 9,515,339 B2
(45) Date of Patent: Dec. 6, 2016

(54) FUEL CELL SYSTEM ION EXCHANGER

(71) Applicant: HONDA MOTOR CO., LTD., Tokyo (JP)

(72) Inventor: Akihito Yuzuriha, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 14/782,509

(22) PCT Filed: Feb. 20, 2014

(86) PCT No.: PCT/JP2014/054783
§ 371 (c)(1),
(2) Date: Oct. 5, 2015

(87) PCT Pub. No.: WO2014/167908
PCT Pub. Date: Oct. 16, 2014

(65) Prior Publication Data
US 2016/0043421 A1 Feb. 11, 2016

(30) Foreign Application Priority Data
Apr. 10, 2013 (JP) .................................. 2013-082460

(51) Int. Cl.
*H01M 8/06* (2016.01)
*C02F 1/42* (2006.01)
(Continued)

(52) U.S. Cl.
CPC ....... *H01M 8/0687* (2013.01); *H01M 8/04164* (2013.01); *H01M 8/04656* (2013.01);
(Continued)

(58) Field of Classification Search
CPC ............ C02F 1/50; C02F 1/42; Y02E 60/525; H01M 8/0618; H01M 8/0687; H01M 8/04022; H01M 8/04067; H01M 8/04097; H01M 8/04164; H01M 8/04201
See application file for complete search history.

(56) References Cited

U.S. PATENT DOCUMENTS

2012/0013185 A1* 1/2012 Ohashi ..................... B60K 1/04
307/10.1
2012/0264029 A1 10/2012 Takamori et al.

FOREIGN PATENT DOCUMENTS

| JP | 2008-300058 | 12/2008 |
| JP | 2008-300059 | 12/2008 |

(Continued)

OTHER PUBLICATIONS

Japanese Office Action dated Jul. 5, 2016 with partial English Translation, 4 pages.
International Search Report, Date of mailing: Nov. 7, 2014.

*Primary Examiner* — Emily Le
*Assistant Examiner* — Monique Wills
(74) *Attorney, Agent, or Firm* — Rankin, Hill & Clark LLP

(57) ABSTRACT

An ion exchanger includes an apparatus body having a lower filter and an upper filter. Ion exchange resin fills a space between the lower filter and the upper filter. A water supply port is provided at a lower position of the apparatus body, and a water discharge port is provided at an upper position of the apparatus body. An air container is provided at an upper position of the apparatus body, and an electric conductivity meter is provided in the air container at a position above the water discharge port.

4 Claims, 16 Drawing Sheets

(51) Int. Cl.
    *H01M 8/04*     (2016.01)
    *H01M 8/12*     (2016.01)
    *G01N 27/08*     (2006.01)
    *C02F 1/50*     (2006.01)

(52) U.S. Cl.
    CPC ... H01M 8/04686 (2013.01); H01M 8/04776 (2013.01); H01M 8/0606 (2013.01); *C02F 1/42* (2013.01); *C02F 1/50* (2013.01); *C02F 2209/05* (2013.01); *G01N 27/08* (2013.01); *H01M 8/04022* (2013.01); *H01M 8/0432* (2013.01); *H01M 8/04067* (2013.01); *H01M 8/04097* (2013.01); *H01M 8/04201* (2013.01); *H01M 8/0618* (2013.01); *H01M 2008/1293* (2013.01); *H01M 2250/10* (2013.01); *Y02B 90/14* (2013.01); *Y02E 60/50* (2013.01); *Y02E 60/525* (2013.01)

(56) References Cited

FOREIGN PATENT DOCUMENTS

| JP | 2009-009732 | 1/2009 |
|----|-------------|--------|
| JP | 2009-009807 | 1/2009 |
| JP | 2010-033917 | 2/2010 |
| JP | 2012-221903 | 11/2012 |
| JP | 10-2013-0026665 | 3/2013 |

* cited by examiner

⇒ :WATER PASSING DIRECTION

⇒ : WATER PASSING DIRECTION

⇒ :WATER PASSING DIRECTION

FIG. 11

| ELECTRIC CONDUCTIVITY σ | STATUS | DETAILS OF PROCESSING |
|---|---|---|
| MORE THAN 30 μS/cm | CONDENSED WATER | DETERMINE DEGRADATION OF EFFICIENCY<br>DISPLAY<br>STOP POWER GENERATION |
| 5 TO 30 μS/cm | PURE WATER | CONTINUE POWER GENERATION |
| LESS THAN 5 μS/cm | AIR | DETERMINE MIXING OF AIR<br>DISPLAY<br>STOP POWER GENERATION |

⇒ : WATER PASSING DIRECTION

FUEL CELL SYSTEM ION EXCHANGER

TECHNICAL FIELD

The present invention relates to a fuel cell system ion exchanger. Water contained in an exhaust gas discharged from a fuel cell for generating electricity by electrochemical reactions of a fuel gas and an oxygen-containing gas passes through the fuel cell system ion exchanger.

BACKGROUND ART

Typically, a solid oxide fuel cell (SOFC) employs a solid electrolyte of ion-conductive oxide such as stabilized zirconia. The solid electrolyte is interposed between an anode and a cathode to form an electrolyte electrode assembly (MEA). The electrolyte electrode assembly is interposed between separators (bipolar plates). In use, normally, predetermined numbers of the electrolyte electrode assemblies and the separators are stacked together to form a fuel cell stack.

As the fuel gas supplied to the fuel cell, normally, a hydrogen gas produced from hydrocarbon raw material by a reformer is used. In general, in the reformer, a reforming raw gas is obtained from a hydrocarbon raw fuel of a fossil fuel or the like, such as methane or LNG, and the reforming raw gas undergoes steam reforming to produce a reformed gas (fuel gas).

In the above steam reforming, water in correspondence with a quantity of water vapor used in the reforming reaction needs to be supplied. For this purpose, an approach where a required quantity of water is supplied from the outside has been adopted. Alternatively, a water collection approach by condensing the exhaust gas produced as a result of power generation in the fuel cell to achieve perfect circulation (water self-sustaining operation) of water needed for reforming has been drawing attention. In this regard, it is required to remove impurities from the condensed water. Therefore, water treatment equipment, e.g., an ion exchanger has been adopted.

For example, as shown in FIG. 13, a fuel cell system disclosed in Japanese Laid-Open Patent Publication No. 2009-009732 (hereinafter referred to as conventional technique 1) includes a water tank 1$a$, and pure water refined by an unillustrated water treatment unit (ion exchange resin membrane) is supplied to the water tank 1$a$. An intake pipe 2$a$ is provided at the bottom of the water tank 1$a$. The intake pipe 2$a$ is connected to an air return mechanism 3$a$. The air return mechanism 3$a$ is provided between the intake pipe 2$a$ and a water pump 4$a$. The air return mechanism 3$a$ includes an air separator 5$a$ and an air return pipe 6$a$.

If air bubbles are formed in the pure water supplied from the water tank 1$a$ into the intake pipe 2$a$, before the air bubbles reach the water pump 4$a$, the air bubbles are guided into the air return pipe 6$a$, and returned to the water tank 1$a$. According to the disclosure, after the air bubbles are removed from the pure water, the pure water is supplied to the water pump 4$a$.

Further, as shown in FIG. 14, a fuel cell system disclosed in Japanese Laid-Open Patent Publication No. 2010-033917 (hereinafter referred to as conventional technique 2) includes a water purifier 1$b$. Water collected from the fuel cell system is guided into the water purifier 1$b$, and purified in the water purifier 1$b$ to produce pure water. The water purifier 1$b$ includes a container 4$b$ filled with ion exchange resin 2$b$ for producing pure water from the collected water and antibacterial agent 3$b$ having a predetermined thickness above the ion exchange resin 2$b$ in the direction of gravity.

The water purifier 1$b$ is an apparatus for producing pure water from the collected water supplied from a condenser (not shown). The pure water produced from the collected water in the water purifier 1$b$ flows through a water passing pipe 5$b$, and the pure water is supplied to a water storage 6$b$.

Further, as shown in FIG. 15, a fuel cell device disclosed in Japanese Laid-Open Patent Publication No. 2008-300058 (hereinafter referred to as conventional technique 3) includes a condensed water tank 1$c$ for storing condensed water produced by heat exchange in a heat exchanger (not shown). An end of a condensed water supply pipe 2$c$ is connected to a lower end of the condensed water tank 1$c$, and the condensed water supply pipe 2$c$ is connected to the heat exchanger. A water tank 4$c$ is connected to an upper end of the condensed water tank 1$c$ through a tank coupling pipe 3$c$. The condensed water tank 1$c$ contains, e.g., ion exchange resin 5$c$ as means for treatment of the condensed water.

Further, as shown in FIG. 16, a fuel cell device disclosed in Japanese Laid-Open Patent Publication No. 2008-300059 (hereinafter referred to as conventional technique 4) includes a condensed water tank 1$d$. After the condensed water stored in the condensed water tank 1$d$ is treated by condensed water treatment means (e.g., ion exchange resin) 2$d$, the condensed water flows through a tank coupling pipe 3$d$, and the condensed water is supplied to a water tank 4$d$. The water stored in the water tank 4$d$ is supplied to a reformer (not shown) in correspondence with the quantity of water required in the reformer.

The condensed water tank 1$d$ includes an upper partition member 5$d$ and a lower partition member 6$d$. For example, the upper partition member 5$d$ and the lower partition member 6$d$ have mesh structure, or the upper partition member 5$d$ and the lower partition member 6$d$ are mesh-like members. The condensed water treatment means 2$d$ is placed between the upper partition member 5$d$ and the lower partition member 6$d$.

SUMMARY OF INVENTION

In the conventional technique 1, the air return mechanism 3$a$ including the air separator 5$a$ and the air return pipe 6$a$ is provided between the water tank 1$a$ and the water pump 4$a$. Therefore, the equipment has a significantly large size as a whole. Further, since the water treatment unit is provided separately, size reduction cannot be achieved. Moreover, when the equipment is configured initially, or in the case where the equipment has not been used for a long period of time, air tends to be stagnant in the air return mechanism 3$a$, and the air cannot be removed reliably.

Further, in the conventional technique 2, since the collected water passes through the water purifier 1$b$ from upper to lower positions, only part of the ion exchange resin 2$b$ tends to be used, and the ion exchange efficiency is low. Moreover, when the purified collected water is guided from the lower position of the water purifier 1$b$ to the water passing pipe 5$b$, broken pieces or powder of the ion exchange resin 2$b$ may be mixed into the collected water guided from the water purifier 1$b$.

Further, in the conventional technique 3, in the case where the air is mixed into the device initially, the air tends to be stagnant at an upper portion of the condensed water tank 1$c$. Therefore, since the air is mixed into the condensed water supplied from the condensed water tank 1$c$ to the water tank 4$c$, it is not possible to supply a stable and correct quantity of the reforming water.

Further, in the condensed water tank 1$c$ containing the ion exchange resin 5$c$, the treated water is sent to the water tank 4c through the tank coupling pipe 3c provided at the upper position of the condensed water tank 1c. Therefore, for example, dust particles or the like floating inside the condensed water tank 1c may be sent to the water tank 4c undesirably.

Furthermore, in the conventional technique 4, since the condensed water passes through the condensed water tank 1d from upper to lower positions, the ion exchange efficiency of the condensed water treatment means 2d is low. Moreover, since the condensed water treatment means 2d is placed between the upper partition member 5d and the lower partition member 6d such as meshes, it becomes difficult to suppress mixing of foreign materials into the reforming water (treated water).

The present invention has been made to solve the problem of this type, and an object of the present invention is to provide a fuel cell system ion exchanger which makes it possible to achieve improvement in the ion exchange efficiency, improvement in the durability, reduction in the number of components, and reduction in the number of steps of maintenance operation.

The present invention relates to a fuel cell system ion exchanger for passing water therethrough. The water is contained in an exhaust gas discharged from a fuel cell for generating electricity by electrochemical reactions of a fuel gas and an oxygen-containing gas.

This ion exchanger includes an apparatus body having internal filters at upper and lower positions. Ion exchange resin fills a space between the filters. A water supply port is provided at a lower position of the apparatus body, for supplying the water into the ion exchange resin. A water discharge port is provided at an upper position of the apparatus body, for discharging the water which has passed through the ion exchange resin. An air container is provided at an upper position of the apparatus body, for containing the air mixed into the apparatus body in a concentrated manner. An electric conductivity measuring unit is provided in the air container at a position above the water discharge port, for measuring electric conductivity of the water which passed through the ion exchange resin.

In the present invention, the water supply port is provided at the lower position of the apparatus body, and the water discharge port is provided at the upper position of the apparatus body. In the structure, since the water flows inside the apparatus body, from lower to upper positions, i.e., in the direction opposite to the gravity direction, non-uniform flow of the water within the apparatus body is suppressed. Further, the time period of contact between the water flowing in the direction opposite to the gravity direction and the ion exchange resin becomes long, and thus, ion exchange is performed reliably to achieve improvement in the ion exchange efficiency.

Further, the air container is provided at the upper position of the apparatus body, for containing the air mixed into the apparatus body in a concentrated manner. In the structure, it is possible to suppress the air from flowing downstream of the ion exchanger. Therefore, it becomes possible to suppress degradation of the performance of the water pump due to air entailment, oxidation of reforming catalyst due to mixing of the air into the reformer, and instability of power generation voltage of the fuel cell due to carbon deposition on the electrodes.

Furthermore, the electric conductivity measuring unit is provided in the air container at the position above the water discharge port, for measuring electric conductivity of the water which has passed through the ion exchange resin. In the structure, the state of purified water and the quantity of water in the apparatus body can be recognized easily and reliably. Reduction in the number of components, and reduction in the number of steps of maintenance operation can be achieved advantageously.

Further, the filters are provided at the upper and lower positions inside the ion exchanger, and the ion exchange resin is provided between the upper and lower filters. Therefore, the lower filter on the upstream side has functions of removing dust particles contained in the condensed water and preventing tiny pieces of the ion exchange resin from flowing upstream of the ion exchanger. The upper filter on the downstream side has a function of preventing tiny pieces of the ion exchange resin from flowing downstream of the ion exchange resin.

BRIEF DESCRIPTION OF DRAWINGS

FIG. 11 is a table illustrating processing of the method;

DESCRIPTION OF EMBODIMENTS

Figure 1:
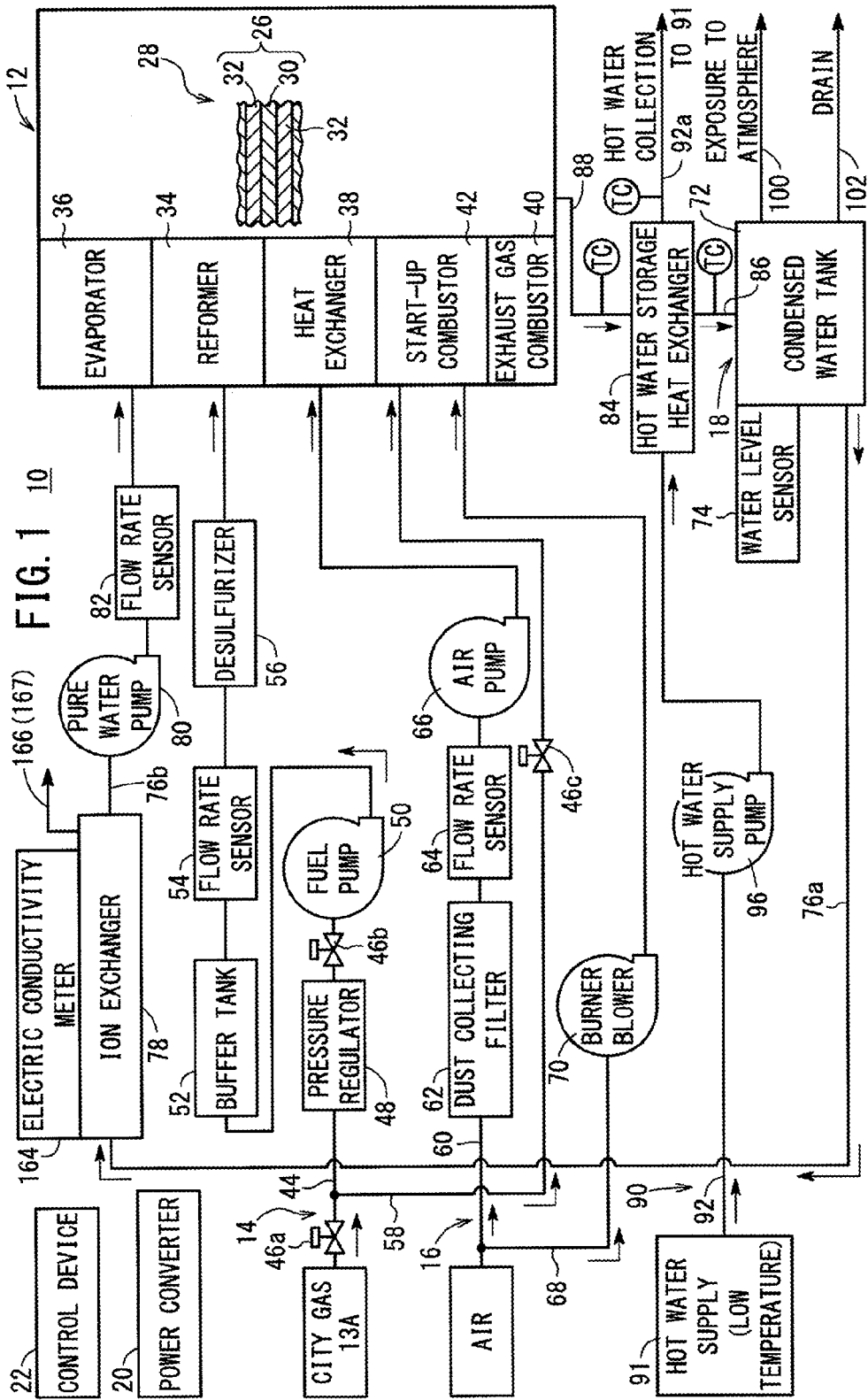
FIG. 1 is a diagram schematically showing structure of a fuel cell system including an ion exchanger according to a first embodiment of the present invention.

As shown in FIG. 1, a fuel cell system 10 including an ion exchanger (described later) according to a first embodiment of the present invention is used in a stationary application. However, the fuel cell system 10 can be used in various applications. For example, the fuel cell system 10 may be mounted in a vehicle.

The fuel cell system 10 includes a fuel cell module (SOFC module) 12 for generating electrical energy in power generation by electrochemical reactions of a fuel gas (e.g., mixed gas of a hydrogen gas, methane, and carbon monoxide) and an oxygen-containing gas (e.g., air), a fuel gas supply apparatus 14 for supplying a raw fuel (e.g., city gas) chiefly containing hydrocarbon as the fuel gas to the fuel cell module 12, an oxygen-containing gas supply apparatus 16 for supplying the oxygen-containing gas to the fuel cell module 12, a water supply apparatus 18 for supplying water to the fuel cell module 12, a power converter 20 for converting the direct current electrical energy generated in the fuel cell module 12 to electrical energy according to the requirements specification, and a control device 22 for controlling the amount of electrical energy generated in the fuel cell module 12. The fuel cell module 12, the fuel gas supply apparatus 14, the oxygen-containing gas supply apparatus 16, the water supply apparatus 18, the power converter 20, and the control device 22 are disposed in a single casing 24 (see FIGS. 2 to 4).

As shown in FIG. 1, the fuel cell module 12 includes a fuel cell stack 28 formed by stacking a plurality of solid oxide fuel cells 26 in a vertical direction (or in a horizontal direction). The fuel cells 26 are formed by stacking electrolyte electrode assemblies (MEA) 30 and separators 32. Though not shown, each of the electrolyte electrode assemblies 30 includes a cathode, an anode, and a solid electrolyte (solid oxide) interposed between the cathode and the anode. For example, the solid electrolyte is made of ion-conductive oxide such as stabilized zirconia.

The fuel cell module 12 includes a reformer 34 for reforming a mixed gas of a raw fuel and water vapor to produce a fuel gas (reformed gas) and supplying the fuel gas to the fuel cell stack 28, an evaporator 36 for evaporating water and supplying the water vapor to the reformer 34, a heat exchanger 38 for raising the temperature of the oxygen-containing gas by heat exchange with a combustion gas and supplying the oxygen-containing gas to the fuel cell stack 28, an exhaust gas combustor 40 for combusting the fuel gas discharged from the fuel cell stack 28 as a fuel exhaust gas and the oxygen-containing gas discharged from the fuel cell stack 28 as an oxygen-containing exhaust gas to produce the combustion gas, and a start-up combustor 42 for combusting the raw fuel and the oxygen-containing gas to produce the combustion gas.

The fuel gas supply apparatus 14 has a raw fuel channel 44 for supplying a city gas (13A) to the reformer 34. A pair of regulator valves 46a, 46b is provided at positions somewhere in the raw fuel channel 44, and a pressure regulator 48 is interposed between the regulator valves 46a, 46b. In the raw fuel channel 44, a fuel pump 50 is provided downstream of the regulator valve 46b. Further, a buffer tank 52, a flow rate sensor 54, and a desulfurizer 56 are provided downstream of the fuel pump 50, successively. In the raw fuel channel 44, a raw fuel branch channel 58 is provided between the regulator valve 46a and the pressure regulator 48. The raw fuel branch channel 58 is connected to the start-up combustor 42, and a regulator valve 46c is provided somewhere in the raw fuel branch channel 58.

The oxygen-containing gas supply apparatus 16 has an air supply pipe 60. A dust collecting filter 62, a flow rate sensor 64, and an air pump 66 are provided along the air supply pipe 60 from the upstream side to the downstream side. The air supply pipe 60 is connected to the heat exchanger 38. An air branch channel 68 is branched from the air supply pipe 60. A burner blower 70 is provided in the air branch channel 68, and the air branch channel 68 is connected to the start-up combustor 42. For example, the start-up combustor 42 has a burner. As described above, the raw fuel and the air are supplied to the start-up combustor 42.

The water supply apparatus 18 has a condensed water tank 72. A water level sensor 74 is provided at the condensed water tank 72, and a water channel (water supply pipe) 76a is connected to a lower position of the condensed water tank 72. The water channel 76a is connected to an ion exchanger 78, and a pure water channel (water discharge pipe) 76b extends from the ion exchanger 78. The pure water channel 76b is connected to the evaporator 36, and a pure water pump (water pump) 80 and a flow rate sensor 82 are provided at positions somewhere in the pure water channel 76b from the upstream side to the downstream side. A hot water storage heat exchanger 84 is connected to the condensed water tank 72 through a discharge water channel 86. The positions of the condensed water tank 72 and the ion exchanger 78 may be interchangeable.

The hot water storage heat exchanger 84 is connected to the heat exchanger 38 through an exhaust pipe 88. At the heat exchanger 38, a partially-consumed reactant gas discharged from the fuel cell stack 28 (hereinafter also referred to as the exhaust gas or combustion exhaust gas) and the air as heated fluid flow in a counterflow manner for heat exchange between these gases. The exhaust gas after the heat exchange is discharged into the exhaust pipe 88, and the air after the heat exchange is supplied to the fuel cell stack 28 as the oxygen-containing gas.

The hot water storage heat exchanger 84 is connected to a hot water supply pipe 92 extending from a hot water tank (hot water supply tank) 91 of a hot water server 90. A hot water supply pump 96 is provided in the hot water supply pipe 92 for supplying water at low temperature to the hot water storage heat exchanger 84. At the hot water storage heat exchanger 84, heat exchange between the supplied water and the exhaust gas is performed. The heated hot water is returned from a hot water supply pipe 92a to the hot water tank 91. A rated exhaust pipe (pipe which is exposed to the atmosphere during the rated operation) 100 and a drain pipe 102 are connected to the condensed water tank 72.

Figure 2:
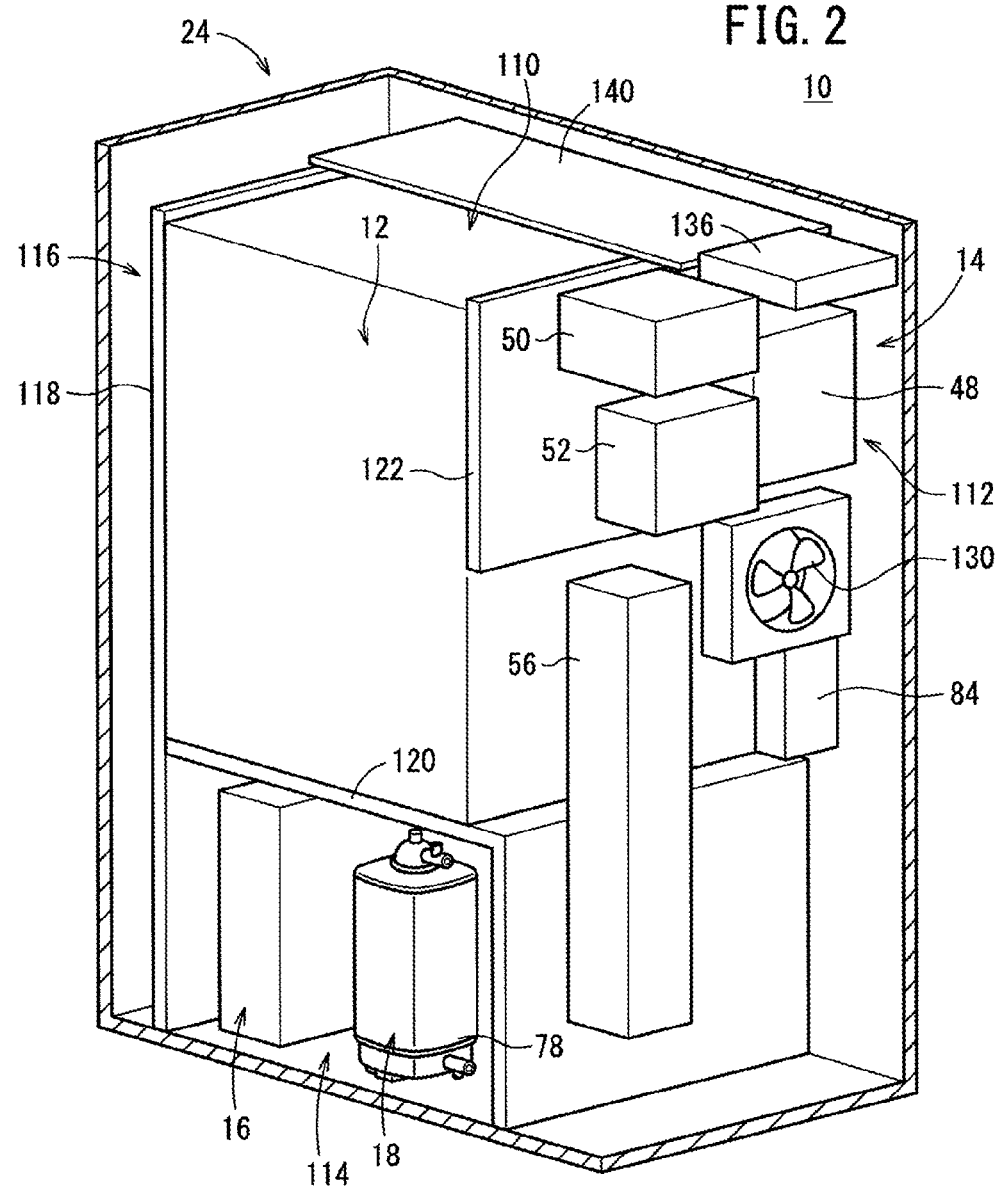
FIG. 2 is a perspective view schematically showing the fuel cell system as viewed from one side of the fuel cell system.
Figure 3:
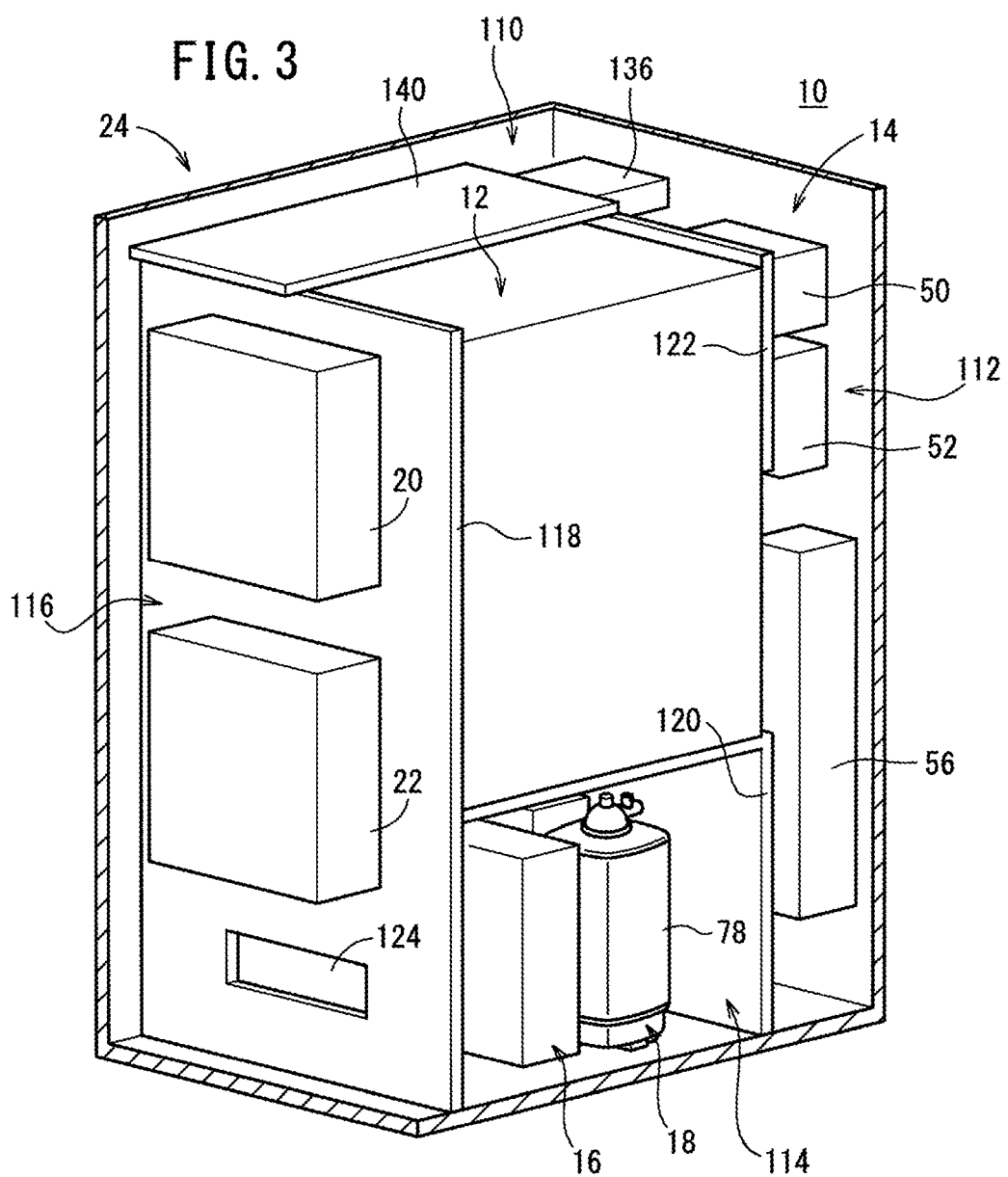
FIG. 3 is a perspective view schematically showing the fuel cell system as viewed from the other side of the fuel cell system.
Figure 4:
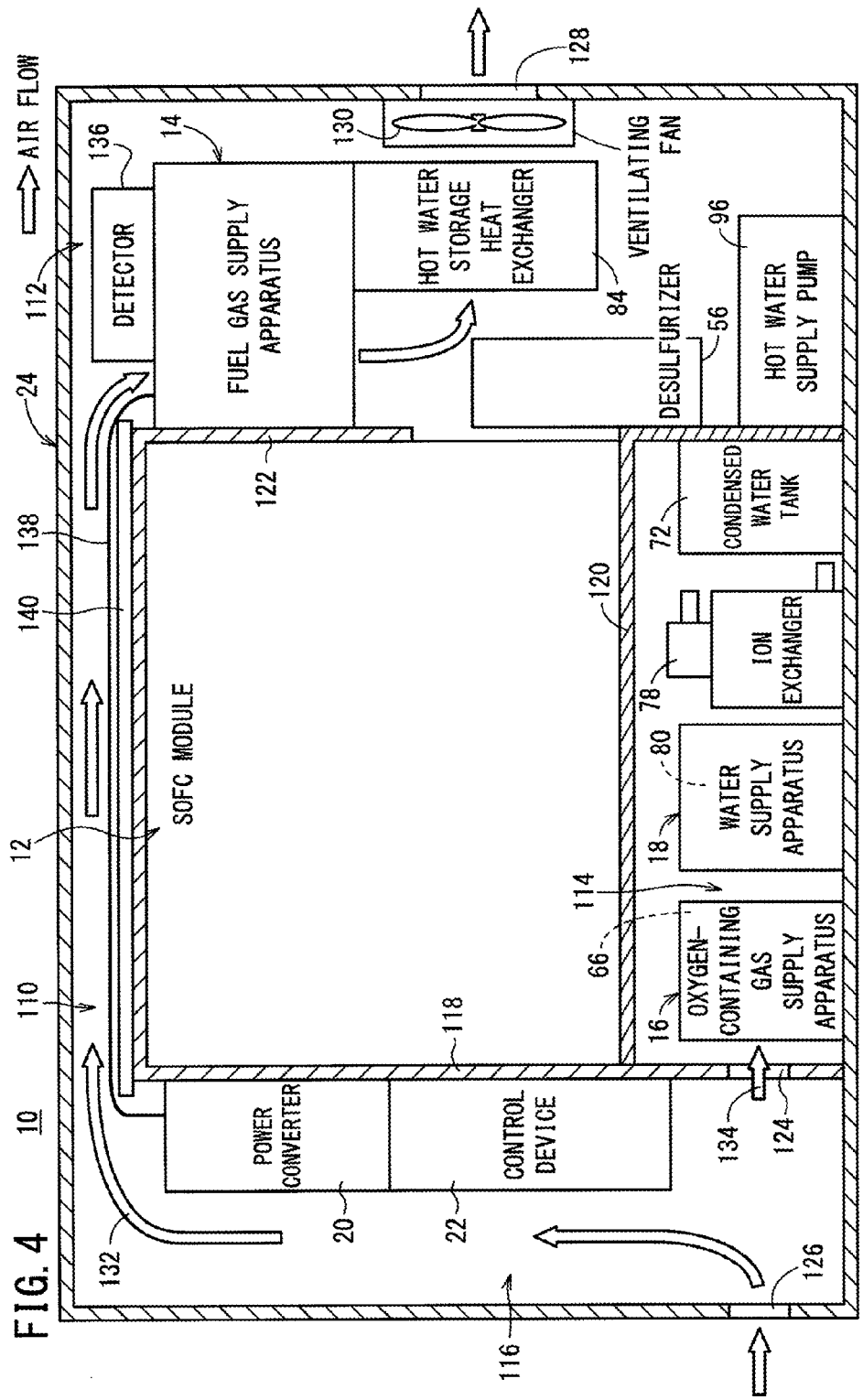
FIG. 4 is a diagram schematically showing the front side of the fuel cell system.

As shown in FIGS. 2 and 3, the casing 24 has a rectangular shape. As shown in FIG. 4, the space in the casing 24 is divided into a module section 110, a first fluid supply section 112, a second fluid supply section 114, and an electrical equipment section 116. The fuel cell module 12 is provided in the module section 110, the fuel gas supply apparatus 14 is provided in the first fluid supply section 112, the oxygen-containing gas supply apparatus 16 and the water supply apparatus 18 are provided in the second fluid supply section 114, and the power converter 20 and the control device 22 are provided in the electrical equipment section 116.

The module section 110, the first fluid supply section 112, the second fluid supply section 114, and the electrical equipment section 116 may be separated from one another using partition members. Alternatively, the module section 110, the first fluid supply section 112, the second fluid supply section 114, and the electrical equipment section 116 may be provided spatially separately in four areas by appearance. A vertical partition plate 118 extending vertically is provided in the casing 24 as a partition of the electrical equipment section 116. A base table 120 having an L-shape in cross section is provided at a lower position of the vertical partition plate 118. A short vertical partition plate 122 is provided adjacent to the first fluid supply section 112.

The module section 110 and the second fluid supply section 114 are provided between the first fluid supply section 112 and the electrical equipment section 116. The second fluid supply section 114 is provided under the module section 110. An air flow port 124 for guiding the air in the electrical equipment section 116 to the second fluid supply section 114 is provided between the electrical equipment section 116 and the second fluid supply section 114, i.e., in the vertical partition plate 118. The electrical equipment section 116 has an air supply port 126 for guiding the air outside the casing 24 into the casing 24. The air supply port 126 is formed in a side surface of the casing 24. The first fluid supply section 112 has an air discharge port 128 and a ventilating fan 130 for guiding the air inside the casing 24 to the outside of the casing 24. The air discharge port 128 is formed in a side surface of the casing 24.

A first ventilating channel 132 and a second ventilating channel 134 are formed inside the casing 24. The first ventilating channel 132 extends from the air supply port 126 to the electrical equipment section 116, an area above the module section 110, the first fluid supply section 112, and the air discharge port 128. The second ventilating channel 134 extends from the air supply port 126 to the electrical equipment section 116, the air flow port 124, and the second fluid supply section 114.

In the first fluid supply section 112, a fuel gas detector 136 for detecting leakage of the fuel gas, the desulfurizer 56 for removing sulfur component from the fuel gas, the fuel gas supply apparatus 14, the hot water storage heat exchanger 84 for performing heat exchange between the exhaust gas discharged from the fuel cell module 12 and the hot water supplied from the hot water tank 91, and the hot water supply pump 96 are provided.

In the second fluid supply section 114, the oxygen-containing gas supply apparatus 16, the condensed water tank 72 for storing condensed water obtained from the exhaust gas discharged from the fuel cell module 12, the ion exchanger 78 for flowing the condensed water, and the water supply apparatus 18 are provided.

In the electrical equipment section 116, the power converter 20 is provided above the control device 22. The ventilating fan 130 is provided between the hot water storage heat exchanger 84 and the air discharge port 128. A beam plate 140 is provided above the module section 110, and a cable 138 connecting the first fluid supply section 112 and the electrical equipment section 116 is placed on the beam plate 140.

The ion exchanger 78 according to the first embodiment is capable of removing impurities from the condensed water to obtain pure water. In addition to dust particles, the impurities herein include substances that are not contained in pure water, e.g., salts such as calcium, magnesium, silica, sodium, and potassium, water soluble electrolyte components, and organic substance.

Figure 5:
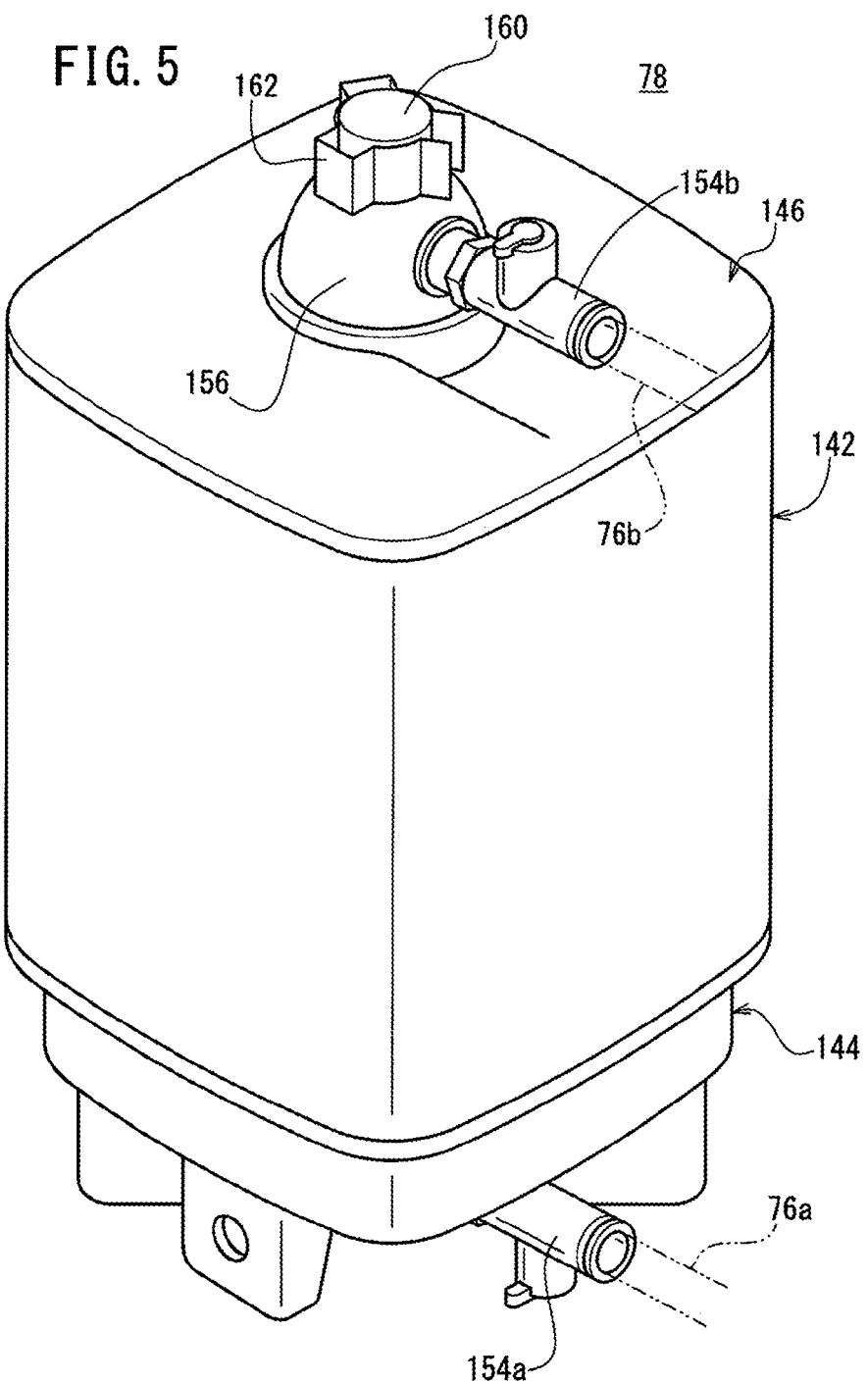
FIG. 5 is a perspective view schematically showing the ion exchanger.
Figure 6:
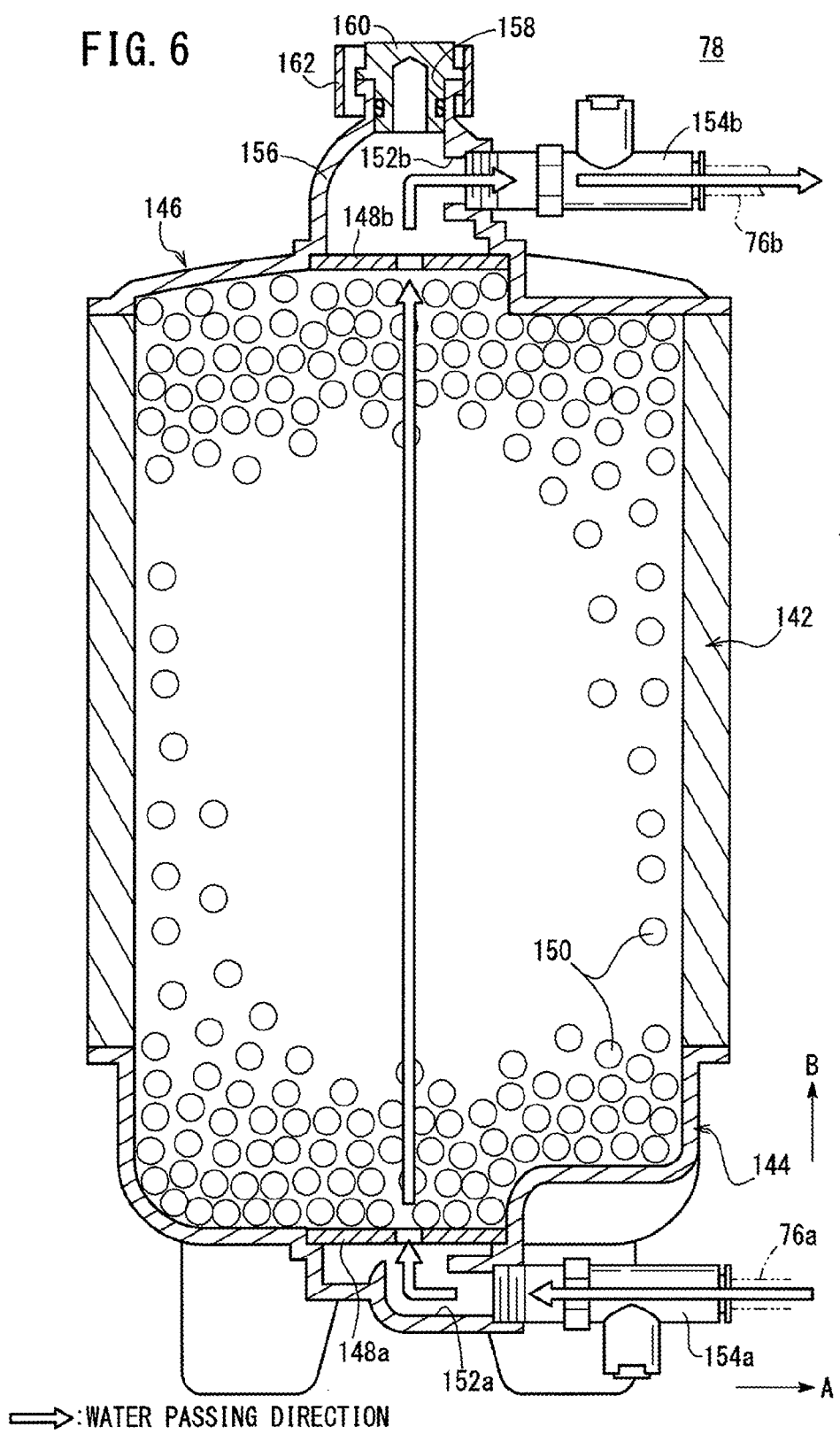
FIG. 6 is a vertical cross sectional view showing the ion exchanger.

As shown in FIGS. 5 and 6, the ion exchanger 78 includes a rectangular cylindrical apparatus body 142. A lower lid member 144 and an upper lid member 146 are attached to a lower end and an upper end of the apparatus body 142, respectively. As shown in FIG. 6, a lower filter 148a and an upper filter 148b are provided inside the apparatus body 142. For example, the lower filter 148a and the upper filter 148b are mesh filters. Particles of ion exchange resin 150 fill a space between the lower filter 148a and the upper filter 148b.

A water supply port 152a is provided at a lower position of the apparatus body 142, i.e., in the lower lid member 144, for supplying water (condensed water) into the ion exchange resin 150. A water discharge port 152b is provided at an upper position of the apparatus body 142, i.e., in the upper lid member 146, for discharging water which has passed through the ion exchange resin 150. The water supply port 152a extends in a horizontal direction (lateral direction) up to a lower central position of the apparatus body 142, and the water supply port 152a is opened upward from the lower central position into the apparatus body 142. This allows the water to flow from the central position of the lower filter 148a.

A water supply seal valve 154a is provided at the water supply port 152a. The water supply seal valve 154a is a one-touch cock for detachably connecting the water channel 76a. A water discharge seal valve 154b is provided at the water discharge port 152b. The water discharge seal valve 154b is a one-touch cock for detachably connecting the pure water channel 76b. The directions in which pipes are detached respectively from the water supply seal valve 154a and the water discharge seal valve 154b are the same (in the direction indicated by the arrow A). The directions in which pipes are connected respectively to the water supply seal valve 154a and the water discharge seal valve 154b are also the same.

An air container 156 is provided at an upper position of the apparatus body 142, i.e., in the upper lid member 146. The air container 156 contains the air mixed into the apparatus body 142 in a concentrated manner. The air container 156 has an upwardly curved dome shape, and the water discharge port 152b extending in the horizontal direction is connected to an upper portion of the air container 156. A connection port 158 is provided in the air container 156, at a position above the water discharge port 152b. The connection port 158 is opened upward in the direction of gravity (in the direction opposite to the gravity direction). A closure cap 160 is attached to the connection port 158, and the closure cap 160 is fixed to the air container 156 using a fixing member 162.

Figure 7:
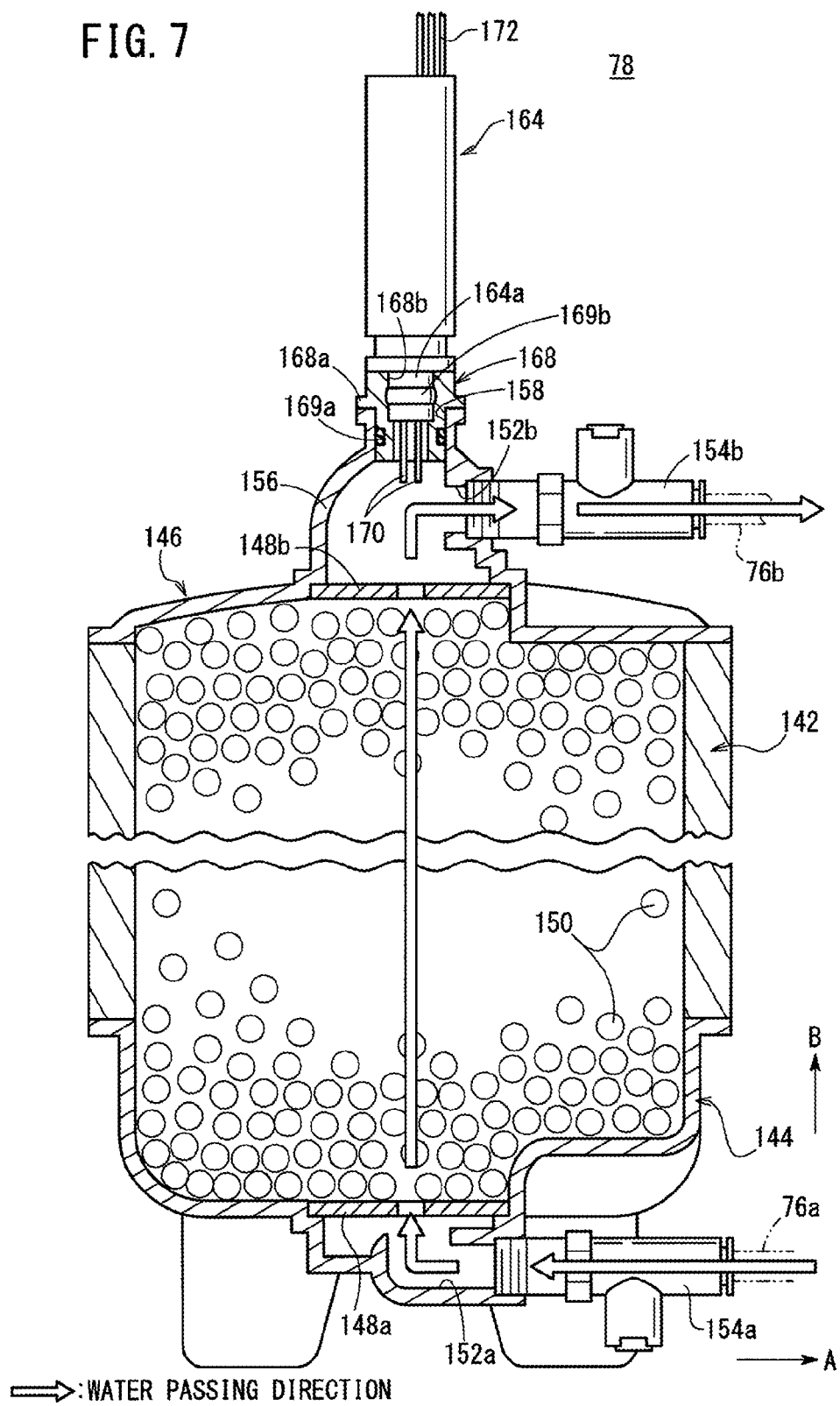
FIG. 7 is a vertical cross sectional view showing a state where an electric conductivity meter is attached to the ion exchanger.
Figure 8:
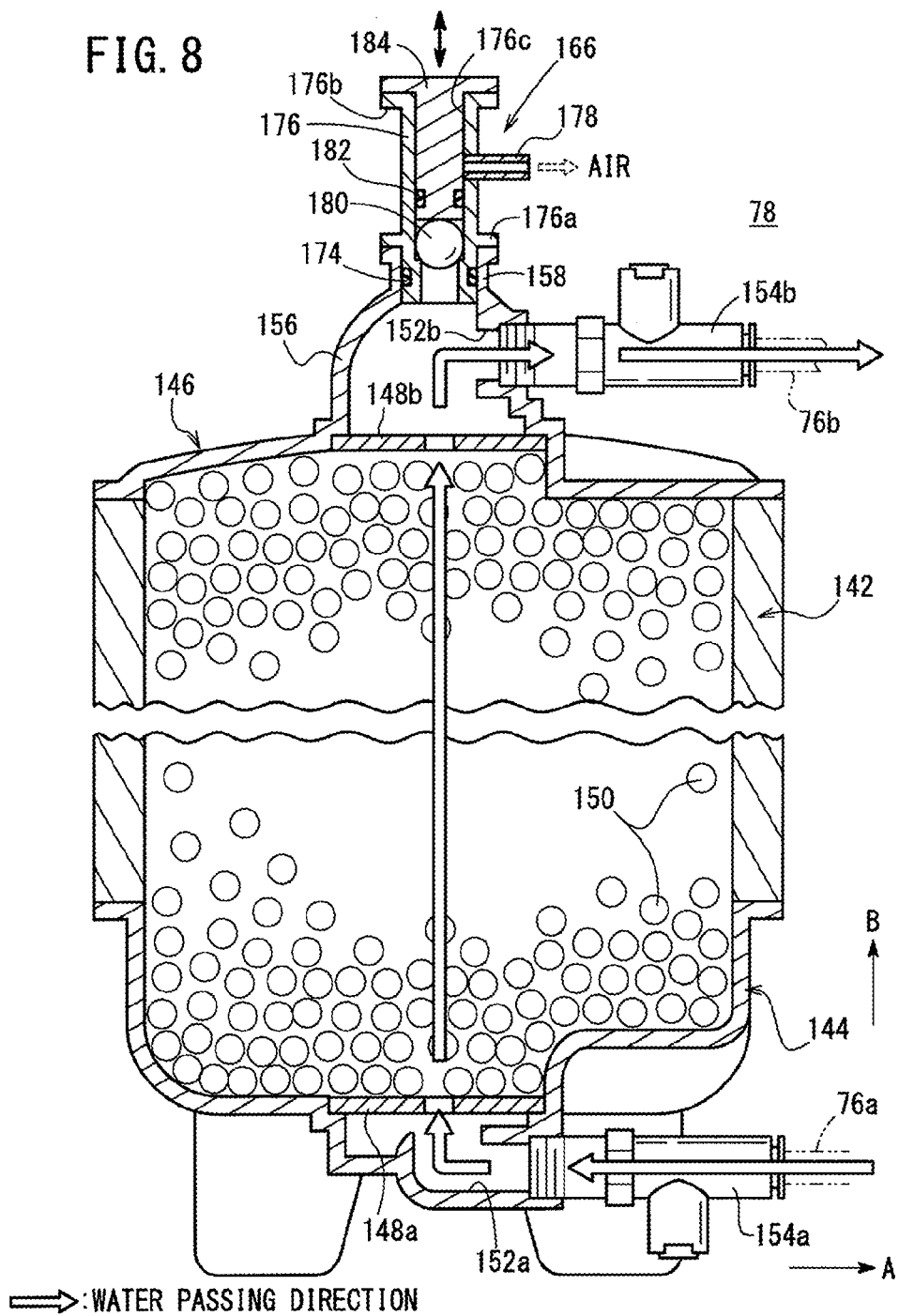
FIG. 8 is a vertical cross sectional view showing a state where an air discharge pipe is attached to the ion exchanger.
Figure 9:
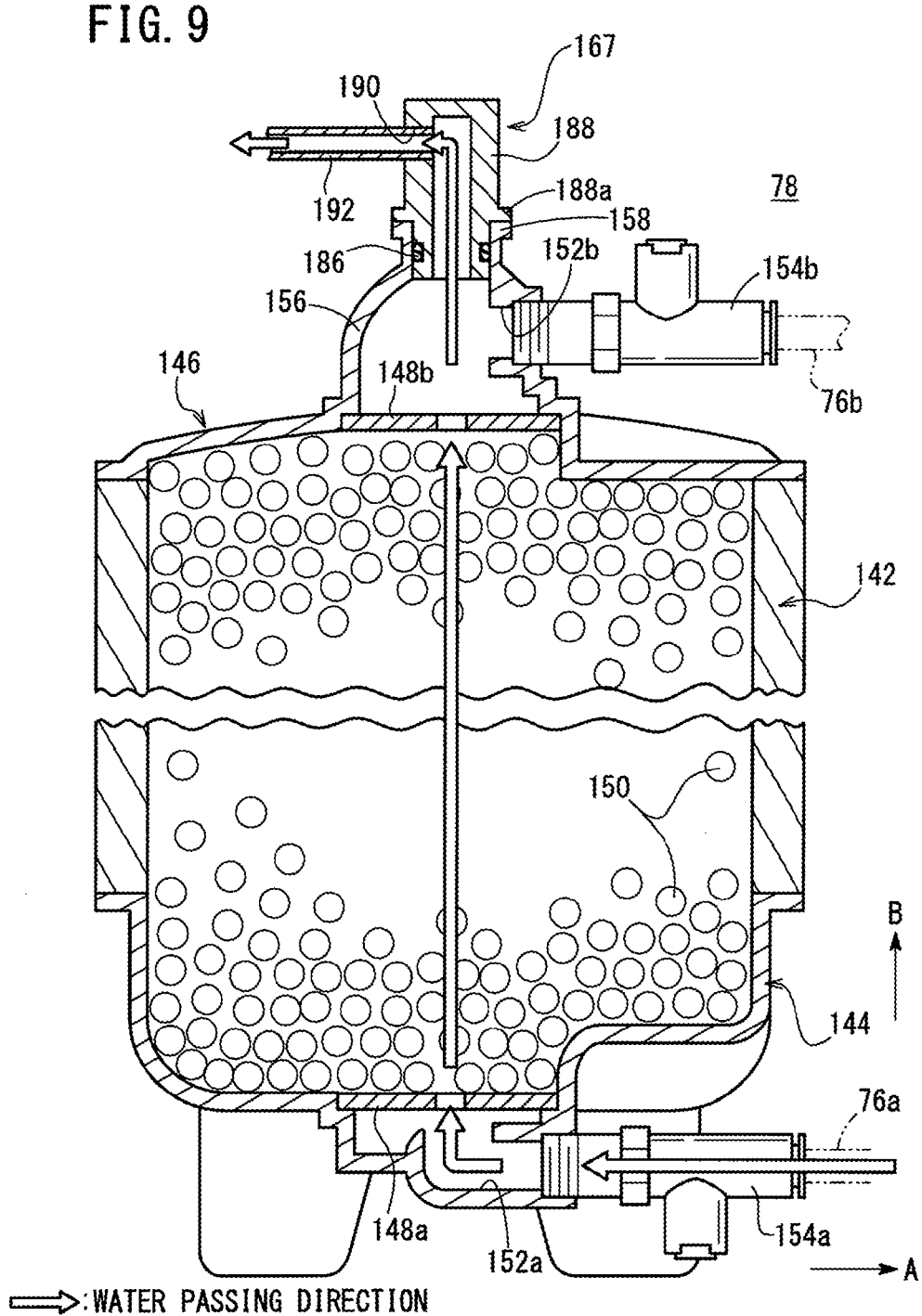
FIG. 9 is a vertical cross sectional view showing a state where a drain discharge pipe is attached to the ion exchanger.

Instead of the closure cap 160, an electric conductivity meter (electric conductivity measuring unit) 164 shown in FIG. 7, an air discharge pipe (excessive fluid discharge pipe) 166 shown in FIG. 8, or a drain discharge pipe (excessive fluid discharge pipe) 167 shown in FIG. 9 is attached to the connection port 158, selectively. The electric conductivity meter 164 has a function of measuring electric conductivity σ of the water which has passed through the ion exchange resin 150. The air discharge pipe 166 has a function of discharging the air from the apparatus body 142, and the drain discharge pipe 167 has a function of discharging the excessive fluid and the air from the apparatus body 142.

As shown in FIG. 7, a coupling cylindrical body 168 is attached to the connection port 158 through an O-ring 169a, and the electric conductivity meter 164 is attached to the coupling cylindrical body 168. The coupling cylindrical body 168 has a flange 168a which contacts an opened end of the connection port 158. A stepped hole 168b is formed in the coupling cylindrical body 168, and a front end 164a of the electric conductivity meter 164 having a small diameter is attached to the stepped hole 168b through an O-ring 169b.

A pair of measurement terminals 170 is provided at the front end 164a of the electric conductivity meter 164. The measurement terminals 170 are exposed to the inside of the air container 156. Preferably, front ends (lower ends) of the measurement terminals 170 are positioned above the water discharge port 152b. A harness 172 is provided at the rear end of the electric conductivity meter 164, and the harness 172 is connected to the control device 22.

As shown in FIG. 8, at the air discharge pipe 166, a cylindrical member 176 is attached to the connection port 158 through an O-ring 174. The cylindrical member 176 includes a flange 176a which contacts the opened end of the connection port 158, and a flange 176b expanded in diameter at its upper end. A discharge channel 178 for releasing air is provided between the flanges 176a, 176b. The discharge channel 178 is opened to the outside.

A stepped hole 176c is formed in the cylindrical member 176, and a ball 180 is provided in the stepped hole 176c. The ball 180 contacts a step of the stepped hole 176c to disconnect the air container 156 from the discharge channel 178. A piston 184 is positioned in the stepped hole 176c through an O-ring 182. The piston 184 is slidable vertically.

Instead of the piston 184, a screw member screwed to a screw groove (not shown) formed in the inner circumferential surface of the stepped hole 176c may be used. Further, instead of the piston 184 which is opened/closed by manual operation, a solenoid valve (not shown) for disconnecting the air container 156 from, and connecting the air container 156 to, the discharge channel 178 may be provided to automatically open/close the channel and release the air depending on the electric conductivity a.

As shown in FIG. 9, the drain discharge pipe 167 includes a cylindrical member 188 attached to the connection port 158 through an O-ring 186. An upper end of the cylindrical member 188 is closed, and the cylindrical member 188 has a flange 188a which contacts an opened end of the connection port 158. A connection hole 190 is formed at an upper position of the cylindrical member 188. The connection hole 190 extends into the cylindrical member 188, and passes through the cylindrical member 188 in a horizontal (radial direction). One end of a drain pipe 192 is connected to the connection hole 190, and the other end of the drain pipe 192 is connected to, e.g., the condensed water tank 72.

Operation of the fuel cell system 10 will be described below.

As shown in FIG. 1, at the time of starting operation of the fuel cell system 10, by operation of the fuel gas supply apparatus 14, for example, a raw fuel such as the city gas (including $CH_4$, $C_2H_6$, $C_3H_8$, $C_4H_{10}$) is supplied to the raw fuel channel 44. The raw fuel from the raw fuel channel 44 flows through the raw fuel branch channel 58, and the raw fuel is supplied to the start-up combustor 42. In the meanwhile, in the oxygen-containing gas supply apparatus 16, by operation of the burner blower 70, the air flows through the air branch channel 68, and the air is supplied to the start-up combustor 42.

Therefore, the mixed gas of the raw fuel and the air is supplied into the start-up combustor 42, and the mixed gas is ignited to start combustion. Thus, the combustion gas is supplied to the heat exchanger 38, the reformer 34, and the evaporator 36 to heat (raise the temperature of) the heat exchanger 38, the reformer 34, and the evaporator 36.

Then, in the fuel gas supply apparatus 14, the fuel pump 50 is driven to supply the raw fuel from the raw fuel channel 44 to the desulfurizer 56. After sulfur is removed from the raw fuel at the desulfurizer 56, the raw fuel is supplied to the reformer 34. In the water supply apparatus 18, the water supplied to the pure water channel 76b through the pure water pump 80 is evaporated by the evaporator 36, and the water vapor is supplied to the reformer 34.

The mixed fuel of the raw fuel and the water vapor undergoes steam reforming in the reformer 34. Thus, hydrocarbon of $C_{2+}$ is removed (reformed), and a reformed gas chiefly containing methane is obtained. The reformed gas is supplied to the fuel cell stack 28. Thus, the methane in the reformed gas is reformed, and the hydrogen gas is obtained. The fuel gas chiefly containing the hydrogen gas is supplied to the anodes (not shown).

In the oxygen-containing gas supply apparatus 16, by operation of the air pump 66, the air is supplied to the air supply pipe 60. This air is supplied to the heat exchanger 38. While the air is moving along the heat exchanger 38, heat exchange between the air and the exhaust gas as described later is performed, and the air is heated to the determined temperature beforehand. The air heated by the heat exchanger 38 flows into the fuel cell stack 28, and the air is supplied to cathodes (not shown).

Thus, in each of the electrolyte electrode assemblies 30, electrochemical reactions of the fuel gas and the air are induced for generating electricity. The hot exhaust gas (at several hundred ° C.) discharged from each of the electrolyte electrode assemblies 30 flows through the heat exchanger 38 for heat exchange with the air. The exhaust gas heats the air to a desired temperature, and the temperature of the exhaust gas is decreased.

The exhaust gas is supplied to the evaporator 36 to evaporate water. After the exhaust gas passes through the evaporator 36, the exhaust gas is supplied to the hot water storage heat exchanger 84 through the exhaust pipe 88. Water at low temperature is supplied from the hot water tank 91 of the hot water server 90 to the hot water storage heat exchanger 84. In the hot water server 90, by operation of the hot water supply pump 96, water is supplied to the hot water supply pipe 92. The water flows into the hot water storage heat exchanger 84 for heat exchange with the exhaust gas. Thus, the heated hot water returns from the hot water supply pipe 92a to the hot water tank 91, and the hot water is utilized for home use.

Figure 10:
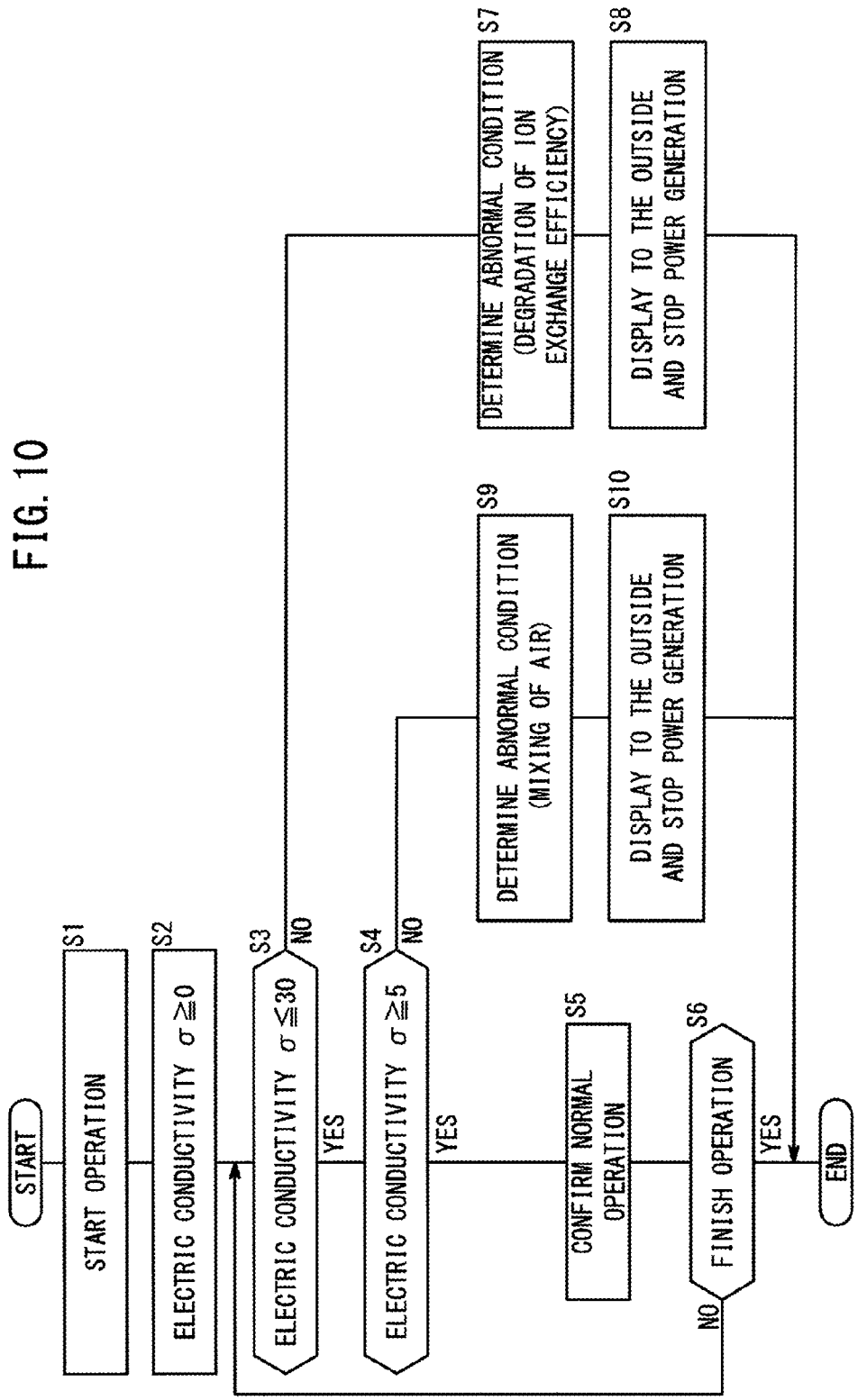
FIG. 10 is a flow chart illustrating a method of detecting a status of the ion exchanger based on the detection result by the electric conductivity meter.

Next, a method of detecting the status (environmental condition) of the ion exchanger 78 based on the detection result obtained by the electric conductivity meter 164 will be described below with reference to a flow chart shown in FIG. 10.

Firstly, in general, if the electric conductivity σ detected by the electric conductivity meter 164 is within a range between 5 μS/cm and 30 μS/cm, pure water is present. If the electric conductivity σ is within a range between 30 μS/cm and 50 μS/cm, condensed water is present. If the electric conductivity σ is less than 0.001 μS/cm, the air is present. S denotes siemens ($1/\Omega$).

In the control device 22, as shown in FIG. 11, the status of the ion exchanger 78 is considered, and details of its processing are determined based on the value of the electric conductivity σ. If the electric conductivity σ is more than 30 μS/cm, it is considered that condensed water (water which has not been subjected to ion exchange) is present, and it is determined that the ion exchange efficiency is degraded. This information is displayed to the outside, and power generation is stopped. If the electric conductivity σ is within a range between 5 μS/cm and 30 μS/cm, it is considered that pure water is present, and power generation is continued. If the electric conductivity σ is less than 5 μS/cm, it is considered that the presence of the air has been detected, and it is determined that mixing of the air has occurred. This information is displayed to the outside, and power generation is stopped.

When operation of the fuel cell system 10 is started (step S1), the routine proceeds to step S2 to detect the electric conductivity σ (≥0) in the air container 156. If it is determined that the electric conductivity σ detected by the electric conductivity meter 164 is 30 μS/cm or less (YES in step S3), the routine proceeds to step S4.

In step S4, if it is determined that the electric conductivity σ detected by the electric conductivity meter 164 is 5 μS/cm or more (YES in step S4), i.e., if the electric conductivity σ is within a range between 5 μS/cm and 30 μS/cm, the routine proceeds to step S5 to confirm that operation is performed normally. Therefore, it is determined that ion exchange of the condensed water is performed properly and the pure water is obtained at the ion exchanger 78. Thus, the power generation is continued until operation is finished (YES in step S6).

In step S3, if it is determined that the electric conductivity σ detected by the electric conductivity meter 164 has exceeded 30 μS/cm (NO in step S3), the routine proceeds to abnormal condition determination in step S7. In this step S7, it is determined that ion exchange efficiency has been degraded (the life of the ion exchange resin 150 has expired). Then, the routine proceeds to step S8 to display this information to the outside, and stop power generation.

Further, in step S4, if it is determined that the electric conductivity σ detected by the electric conductivity meter 164 is less than 5 μS/cm (NO in step S4), the routine proceeds to the abnormal condition determination in step S9. In step S9, it is determined that mixing of the air (shortage of condensed water) has occurred. Then, the routine proceeds to step S10 to display this information to the outside, and stop power generation.

In the first embodiment, as shown in FIG. 6, the water supply port 152a is provided at the lower position of the apparatus body 142, for supplying water into the ion exchange resin 150. Further, the water discharge port 152b is provided at the upper position of the apparatus body 142, for discharging water which has passed through the ion exchange resin 150.

In the structure, since the water flows inside the apparatus body 142, from lower to upper positions, i.e., in the direction (indicated by the arrow B) opposite to the gravity direction, non-uniform flow of the water within the apparatus body 142 is suppressed. Further, the time period of contact between the water flowing in the direction opposite to the gravity direction and the ion exchange resin 150 becomes long, and thus, ion exchange is performed reliably to achieve improvement in the ion exchange efficiency.

Further, the air container 156 is provided at the upper position of the apparatus body 142, for containing the air mixed into the apparatus body 142 in a concentrated manner. In the structure, at the time of initial installation or at the time of replacement, the water and air can be separated, and it becomes possible to prevent the air from flowing downstream of the ion exchanger 78. In particular, since the water discharge port 152b extending in the horizontal direction is connected to the upper position of the air container 156, the pure water mixed with the air is not discharged to the pure water channel 76b significantly. Therefore, it becomes possible to suppress degradation of the performance of the pure water pump 80 due to air entailment, oxidation of reforming catalyst due to mixing of the air into the reformer 34, and instability of power generation voltage of the fuel cell 26, e.g., due to carbon deposition on the electrodes.

Further, as shown in FIG. 7, the electric conductivity meter 164 is provided in the air container 156 at the position above the water discharge port 152b, for measuring the electric conductivity σ of the water which has passed through the ion exchange resin 150. In the structure, the state of purified water and the quantity of water in the apparatus body 142 can be recognized easily and reliably. Reduction in the number of components, and reduction in the number of steps of maintenance operation can be achieved advantageously.

Further, the lower filter 148a and the upper filter 148b are provided inside the apparatus body 142, and the ion exchange resin 150 fills a space between the lower filter 148a and the upper filter 148b. The lower filter 148a is provided above the water supply port 152a, and the upper filter 148b is provided below the water discharge port 152b. Therefore, the ion exchange resin 150 can be reliably held between the lower filter 148a and the upper filter 148b. Further, when the ion exchange resin 150 is degraded, it becomes possible to suppress the damaged portion (e.g., powder) of the ion exchange resin 150 from flowing downstream of the apparatus body 142.

Further, as shown in FIG. 8, instead of the closing cap 160 (or instead of the electric conductivity meter 164), the air discharge pipe 166 for discharging air from the apparatus body 142 is attached to the air container 156 of the ion exchanger 78. At the air discharge pipe 166, when the piston 184 is slided upward within the cylindrical member 176 manually, the ball 180 is lifted to connect the air container 156 and the discharge channel 178. In the structure, the air which is stagnant in the air container 156 flows through the discharge channel 178, and the air is discharged to the outside.

Therefore, it is possible to suppress the air from flowing downstream of the ion exchanger 78. Thus, in the structure, it becomes possible to suppress degradation of the performance of the pure water pump 80 due to air entailment, oxidation of reforming catalyst due to mixing of the air into the reformer 34, and instability of power generation voltage of the fuel cell 26, e.g., due to carbon deposition on the electrodes.

Further, as shown in FIG. 9, instead of the closing cap 160 (or instead of the electric conductivity meter 164 or the air discharge pipe 166), the drain discharge pipe 167 for discharging the excessive water and the air from the apparatus body 142 is attached to the air container 156 of the ion exchanger 78. In the drain discharge pipe 167, in particular, the air which tends to be stagnant in the air container 156 at the time of initial installation is discharged through the drain pipe 192 to the condensed water tank 72 together with the excessive water.

Thus, it is possible to suppress the air from flowing downstream of the ion exchanger 78. In the structure, it becomes possible to suppress degradation of the performance of the pure water pump 80 due to air entailment, oxidation of reforming catalyst due to mixing of the air into the reformer 34, and instability of power generation voltage of the fuel cell 26, e.g., due to carbon deposition on the electrodes.

Further, in the ion exchanger 78, the water supply seal valve 154a is provided at the water supply port 152a, for detachably connecting the water channel 76a, and the water discharge seal valve 154b is provided at the water discharge port 152b for detachably connecting the pure water channel 76b. The directions in which pipes are detached respectively from the water supply seal valve 154a and the water discharge seal valve 154b are the same (in the direction indicated by the arrow A).

In the structure, in the state where the water supply seal valve 154a and the water discharge seal valve 154b are closed, simply by detaching the water channel 76a and the pure water channel 76b in the same direction, the ion exchanger 78 can be replaced easily. Thus, reduction in the number of steps of maintenance operation for the ion exchanger 78 can be achieved reliably.

Further, the ion exchanger 78 is advantageous when it is used for the solid oxide fuel cell 26 where impurities contained in at least water used for steam reforming are removed. However, instead of the solid oxide fuel cell 26, the present invention is also suitably applicable to another type of high temperature fuel cells and medium temperature fuel cells. For example, molten-carbonate fuel cells (MCFC), phosphoric acid fuel cells (PAFC), and hydrogen membrane fuel cells (HMFC) can be adopted suitably.

Figure 12:
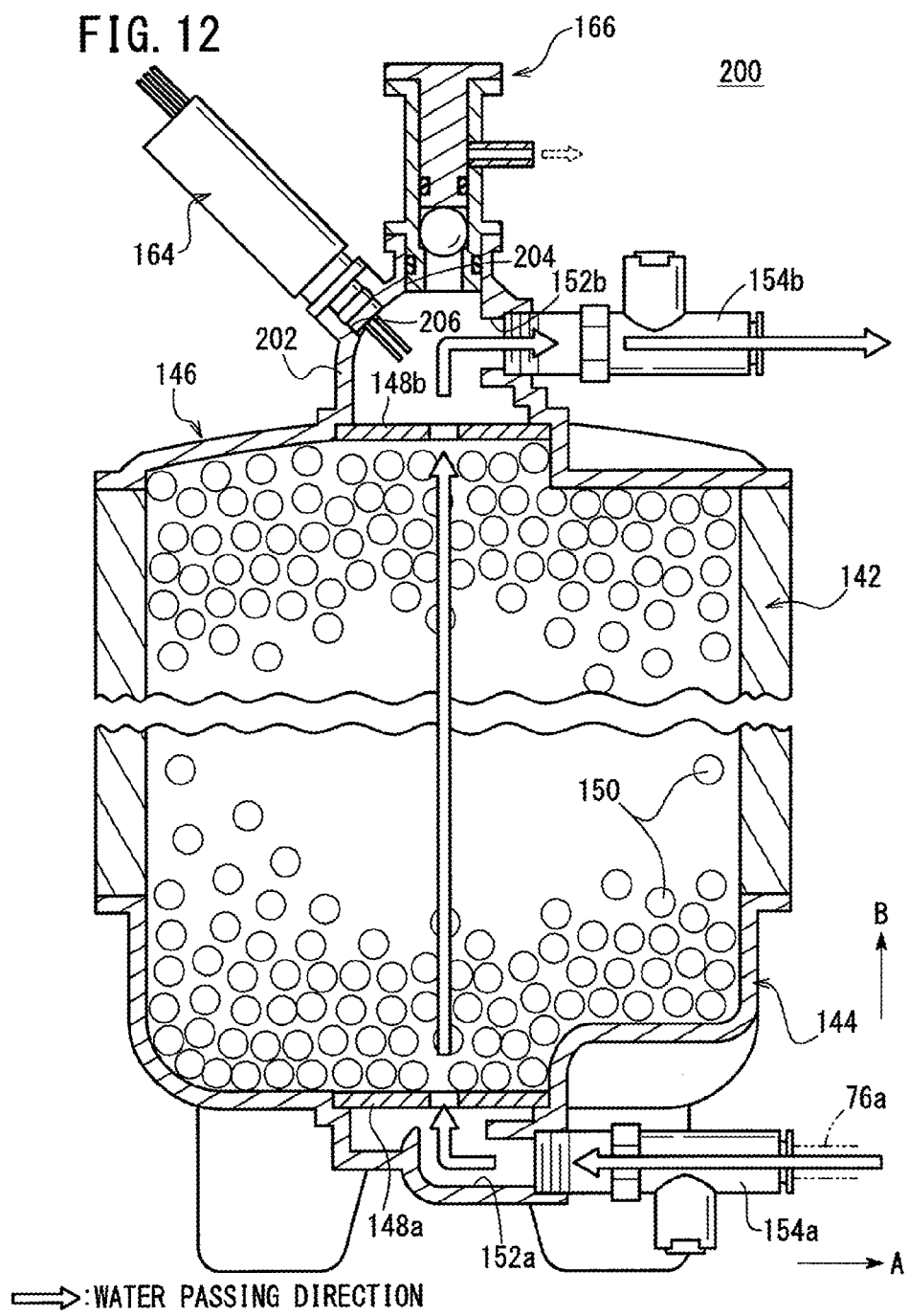
FIG. 12 is a vertical cross sectional view showing an ion exchanger according to a second embodiment of the present invention.
Figure 13:
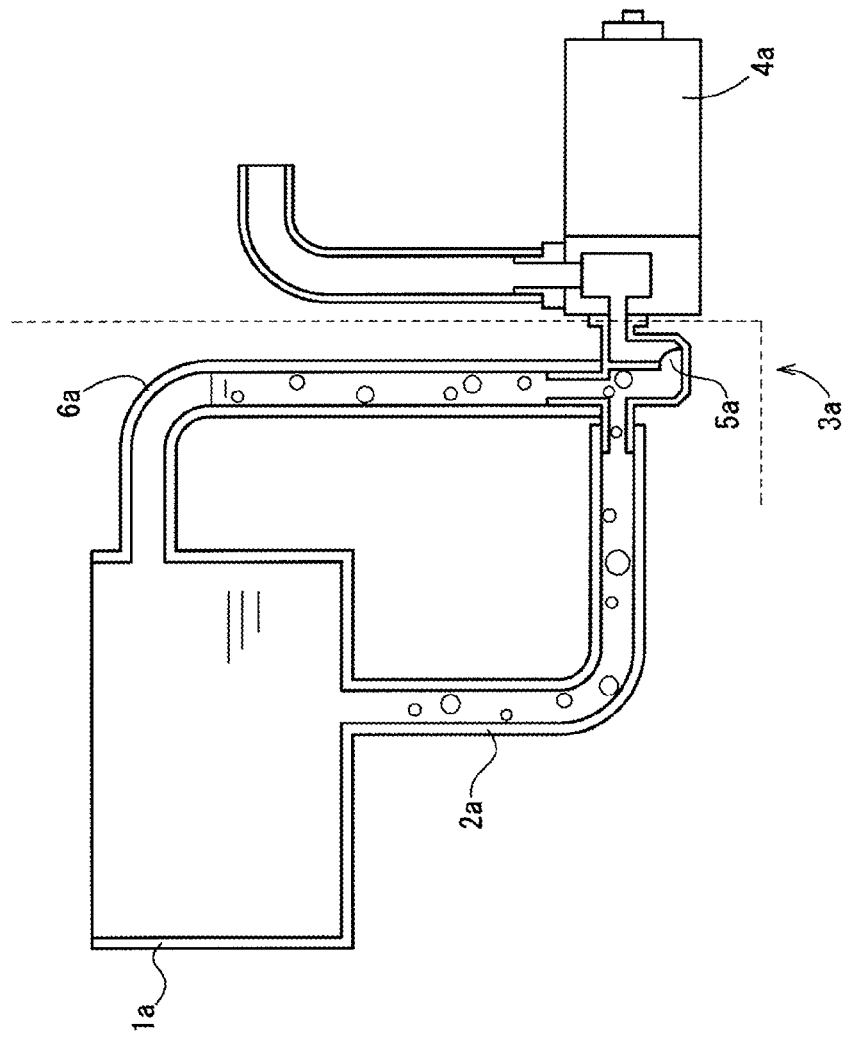
FIG. 13 is a diagram schematically showing structure of a fuel cell system of the conventional technique 1.
Figure 14:
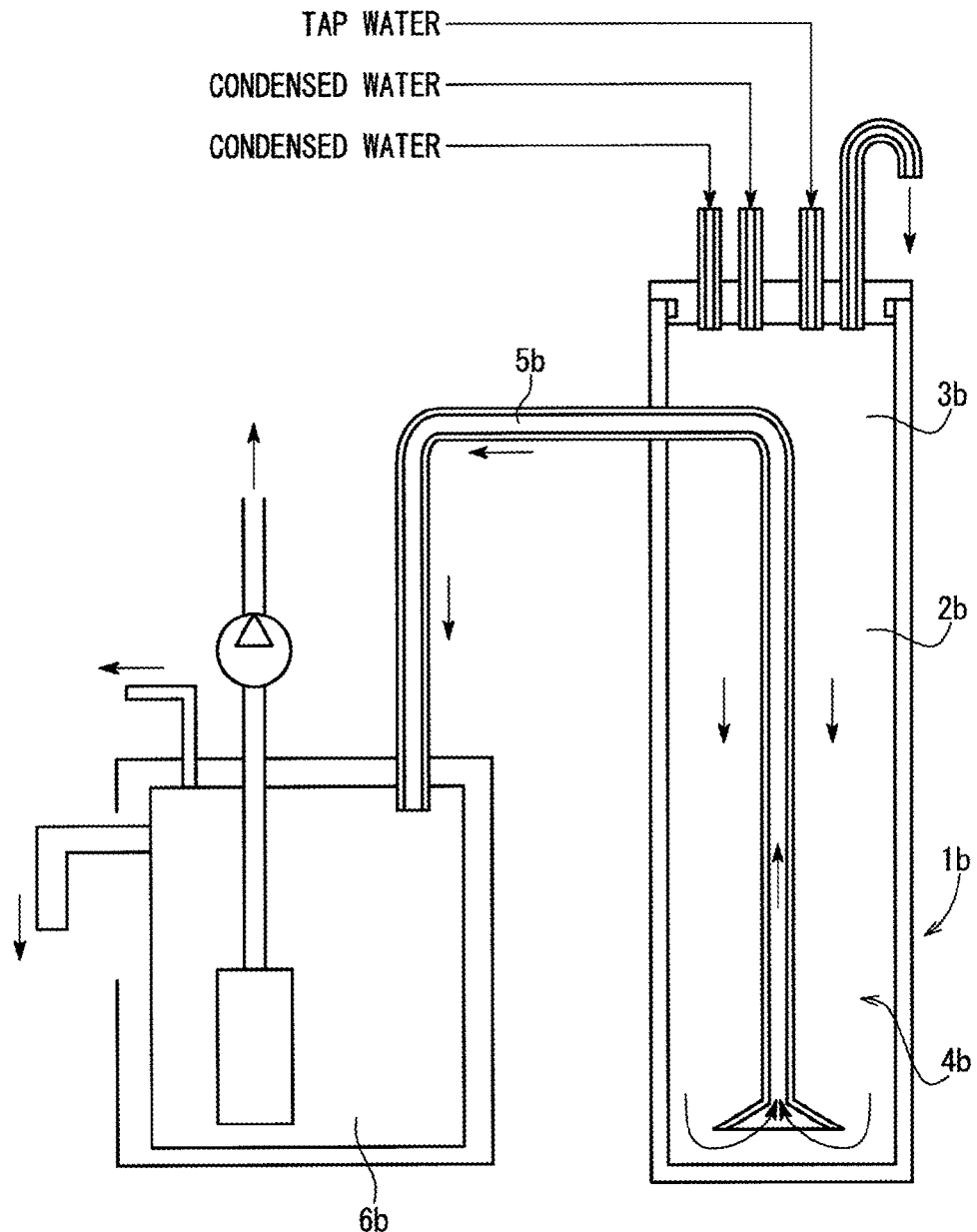
FIG. 14 is a diagram schematically showing structure of a fuel cell system of the conventional technique 2.
Figure 15:
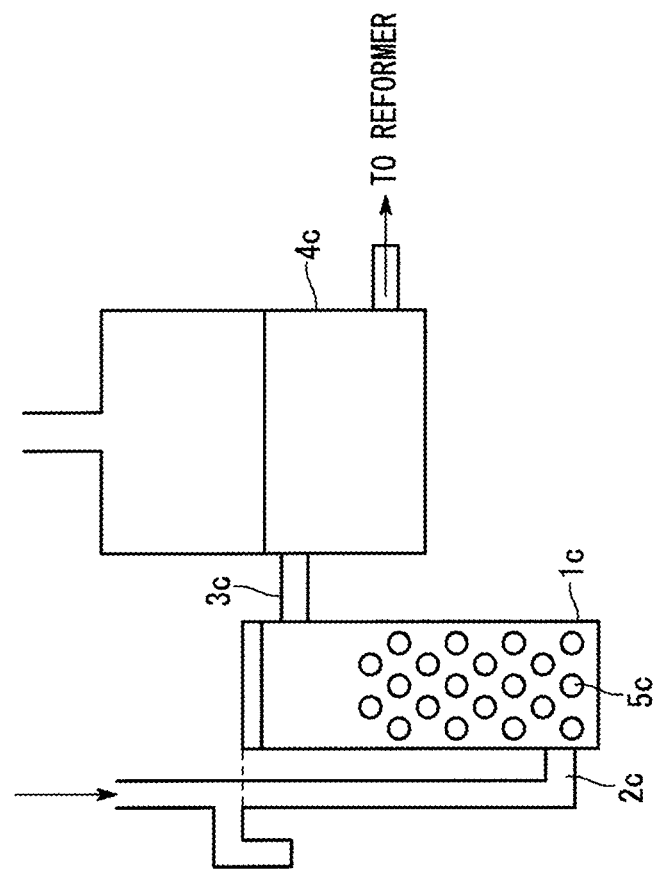
FIG. 15 is a diagram schematically showing structure of a fuel cell device of the conventional technique 3.
Figure 16:
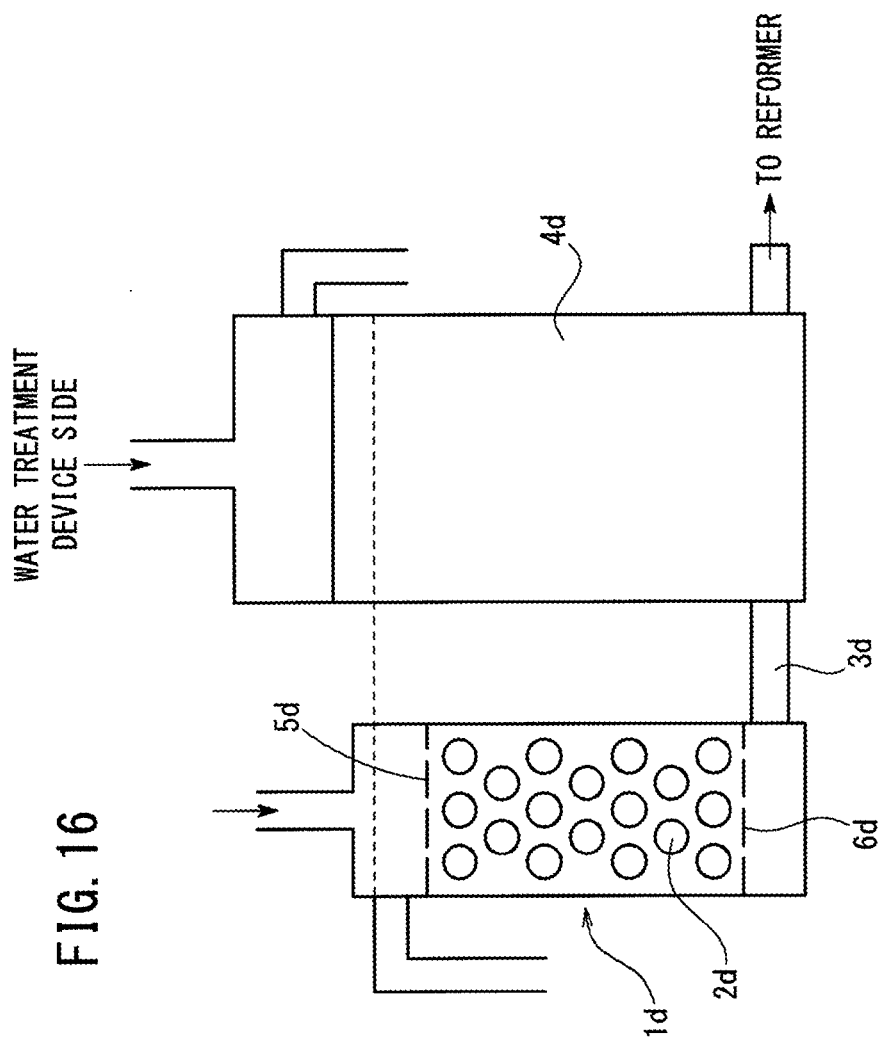
FIG. 16 is a diagram schematically showing structure of a fuel cell device of the conventional technique 4.

FIG. 12 is a vertical cross sectional view showing an ion exchanger 200 according to a second embodiment of the present invention. The constituent elements of the ion exchanger 200 that are identical to those of the ion exchanger 78 according to the first embodiment are labeled with the same reference numerals, and descriptions thereof will be omitted.

An upper lid member 146 of the ion exchanger 200 has an air container 202 containing the air mixed into the apparatus body 142 in a concentrated manner. The air container 202 has a connection port 204 at a position above a water discharge port 152b, and the connection port 204 is opened upward in the direction of gravity. An air discharge pipe 166 (or a drain discharge pipe 167) is attached to this connection port 204. An attachment hole 206 is formed at an upper position of the air container 202 where the attachment hole 206 does not interfere with the air discharge pipe 166. The attachment hole 206 is inclined downward. An electric conductivity meter 164 is attached to the attachment hole 206.

In the second embodiment, the electric conductivity meter 164 and the air discharge pipe 166 are attached to the air container 202. Therefore, the electric conductivity σ of the water which has passed through the ion exchange resin 150 is measured for making it possible to detect stagnation of the air and degradation of the ion exchange efficiency, and discharge the air suitably. Thus, the same advantages as in the case of the first embodiment are achieved. For example, ion exchange is performed reliably to achieve improvement in the ion exchange efficiency, and it becomes possible to suppress instability of the power generation voltage due to air entailment.

The invention claimed is:

1. A fuel cell system ion exchanger for passing water therethrough, the water contained in an exhaust gas discharged from a fuel cell for generating electricity by electrochemical reactions of a fuel gas and an oxygen-containing gas, the fuel cell system ion exchanger comprising:
    an apparatus body having internal filters at upper and lower positions, ion exchange resin filling a space between the filters;
    a water supply port provided at a lower position of the apparatus body, for supplying the water into the ion exchange resin;
    a water discharge port provided at an upper position of the apparatus body, for discharging the water which has passed through the ion exchange resin;
    an air container provided at an upper position of the apparatus body, configured to contain the air mixed into the apparatus body in a concentrated manner;
    an electric conductivity measuring unit provided in the air container at a position above the water discharge port, configured to measure electric conductivity of the water which passed through the ion exchange resin.

2. The fuel cell system ion exchanger according to claim 1, further comprising an excessive fluid discharge pipe provided at the air container, for discharging at least the air from inside of the apparatus body.

3. The fuel cell system ion exchanger according to claim 1, further comprising:
    a water supply seal valve provided at the water supply port, for connecting a water supply pipe detachably; and
    a water discharge seal valve provided at the water discharge port, for connecting a water discharge pipe detachably,
    wherein directions in which pipes are detached respectively from the water supply seal valve and the water discharge seal valve are same, and directions in which the pipes are connected respectively to the water supply seal valve and the water discharge seal valve are same.

4. The fuel cell system ion exchanger according to claim 1, wherein the ion exchanger is applicable to a solid oxide fuel cell, for removing impurities contained in at least water used for steam reforming.

* * * * *